United States Patent [19]

Ty

[11] 4,254,768

[45] Mar. 10, 1981

[54] HYPODERMIC SYRINGE

[76] Inventor: Perla J. Ty, 3640 "B" S. Main St., Santa Ana, Calif. 92707

[21] Appl. No.: 75,836

[22] Filed: Sep. 14, 1979

Related U.S. Application Data

[63] Continuation-in-part of Ser. No. 844,074, Oct. 10, 1977, abandoned.

[51] Int. Cl.³ .............................................. A61M 5/00
[52] U.S. Cl. ............................. 128/218 M; 128/272.1
[58] Field of Search ............ 128/218 M, 218 R, 272.1

[56] References Cited

U.S. PATENT DOCUMENTS

| | | | |
|---|---|---|---|
| 3,016,896 | 1/1962 | Sickle | 128/218 M |
| 3,255,752 | 6/1966 | Dick | 128/218 M |
| 3,279,654 | 10/1966 | Pierick | 128/218 M X |
| 3,337,041 | 8/1967 | Damaskus | 128/218 M |
| 3,348,546 | 10/1967 | Roberts et al. | 128/218 M |
| 3,756,390 | 9/1973 | Abbey et al. | 128/218 M |

Primary Examiner—John D. Yasko

Attorney, Agent, or Firm—Willie Krawitz

[57] ABSTRACT

A multiple barrel hypodermic syringe is provided for mixing materials contained in the barrels prior to use. A typical two barrel syringe comprises a lower barrel for containing a sterile material such as a lyophilizable product, and an upper barrel containing a liquid diluent. The two barrels can be completely disengaged for separate replacement, alteration or reconstitution, etc., of their contents, if necessary.

One or more slot vents are provided along either barrel to enable release of air, gas, moisture, etc., within the lower barrel when they are partially engaged. Upon further engagement in a sterile environment, the slot vents will be totally occluded by the mating surfaces of the two barrels; this enables the syringe to be sealed and the contents stored for future use.

The hypodermic syringe of this invention also enables a lyophilization process to be carried out in situ followed by storage.

9 Claims, 4 Drawing Figures

HYPODERMIC SYRINGE

BACKGROUND OF THE INVENTION

This invention relates to a hypodermic syringe, and more specifically to a multi barrel syringe whose components can be disengaged so that the contents may be reconstituted, replaced, reworked, etc. This application is a continuation-in-part of U.S. Ser. No. 844,074 filed Oct. 10, 1977 now abandoned.

Certain types of pharmaceuticals are solid materials which, prior to injection from a hypodermic syringe, may be dissolved in an inert carrier or a carrier having additional pharmaceutical properties. Typical solids are lyophilized substances such as toxins, antitoxins, serums, etc., which have been prepared in the dry state by quick freezing and dehydration under vacuum; frequently, these pharmaceuticals are stored in the hypodermic syringe itself.

Although lyophilized and other types of solids may be preserved in a hypodermic syringe for long periods of time in a refrigerated and/or sterile condition, problems may arise that necessitate replacement, alteration, or reconstitution of the solid, etc. Some problems which may arise include: (i) power supply variations that can cause the regrigeration temperature to cycle; (ii) the particular solid pharmaceutical might have been partly or wholly defective; (iii) or contain too low (or too high) a dosage content; (iv) or the pharmaceutical may have been improperly weighed; (v) or it might be affected by evaporation-condensation cycles; etc. In other instances it might be desireable to mix a new variation of a pharmaceutical (e.g. a toxin) with an old variety, even if the latter has its original potency.

In addition, it is often necessary to pre-mix one or more solids and liquids so that the solids have sufficient time to be dissolved before being administered to the patient. If the mixing step is accompanied by the entrance of non-sterile air into the chamber, the syringe must be discarded. Also, it might be desireable, from a use and a packaging standpoint, to lyophilize a material in situ in a hypodermic syringe and store the syringe prior to use, e.g. for large scale innoculations, etc.

Finally, in other cases, it may be desireable to simply store a liquid rather than a solid pharmaceutical in the syringe for convenience in packaging. Obviously, use of a stored liquid may have the same or similar problems as a solid.

Consequently, a need exists for a simple and inexpensive hypodermic syringe which can overcome the foregoing problems and fulfill the stated requirements.

THE INVENTION

According to the invention, a multi barrel hypodermic syringe is provided comprising a lower barrel having an outlet port for a hypodermic needle; an upper barrel containing a removeable hypodermic plunger; the upper and lower barrels being sized for sliding engagement and disengagement along their respective outer and inner peripheries; and, one or more vent slots extending along a barrel periphery to permit gas, air and moisture to escape from the lower barrel during lyophilization when the barrels are partly engaged; the vent slots being occluded by the barrel surfaces to seal the lower barrel and its contents when the two barrels are substantially engaged; the upper and lower barrels being adapted to contain a liquid or solid, whereby disengagement of the barrels and plunger enables separate removal and replacement of the liquid or solid from its respective barrel.

The construction of the hypodermic syringe of this invention enables it to be easily handled in a sterile environment and subsequently without contamination of its contents.

DESCRIPTION OF THE PREFERRED EMBODIMENTS

Figures 1, 2, 3:
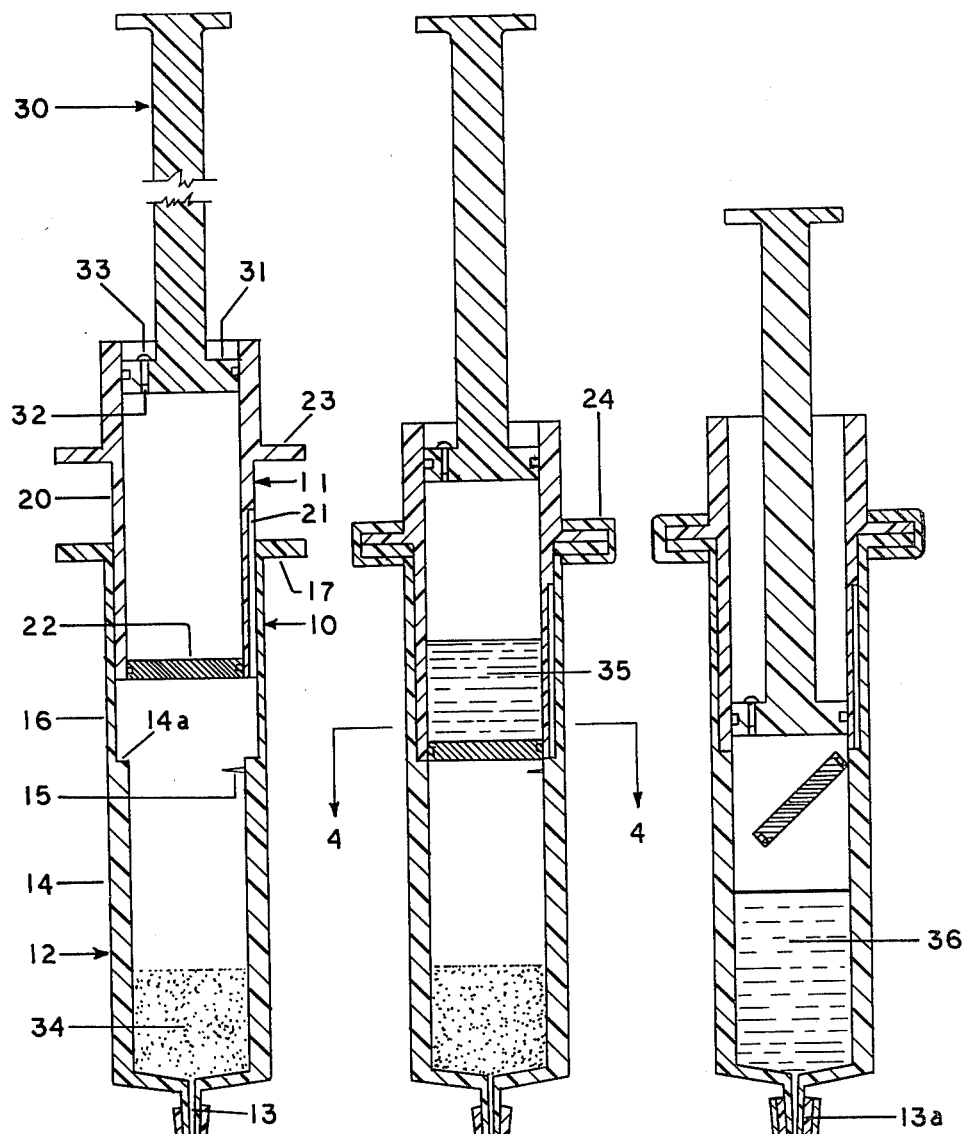
FIGS. 1-3 are axial views in cross sectional side elevation showing a hypodermic syringe of this invention in various stages of operation; and, FIG. 4 is a cross section view, taken along the lines 4—4 of FIG. 2 showing the venting slot arrengement for the lower barrel.

One form of a hypodermic syringe 10 of this invention is shown in FIGS. 1-3 and comprises interfitting and removeable, upper and lower barrels 11, 12. The lower barrel 12 includes an orifice portion 13 with a seal plug 13a, a lower, thick wall portion 14 having an interior shoulder 14a, and a pivot member 15 (also shown in FIG. 4). The upper portion of the lower barrel includes a thin wall member 16 which terminates at the shoulder 14a; the lower barrel 12 is open ended, and an outwardly extending flange 17 is provided thereon. The upper barrel 11 is also open ended with an exterior sidewall 20 that produces a sliding fit with the inner sidewall 16 of the lower barrel 12. A vertical slot 21 is formed along the exterior sidewall and extends from about midway along the upper barrel to its end; the slot 21 provides an air or gas vent from the lower barrel when the two barrels are inserted or closed together.

Figure 4:
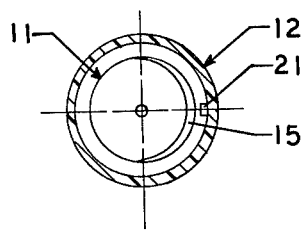

The lower containment end of the upper barrel 11 includes a frangible or removeable bottom portion 22, and, as shown in FIGS. 3 and 4, the bottom 22 is adapted to contact and be disengaged by a pivot member 15. If desired, the containment end of the upper tube 11 may be frangible, and other means can be provided to cause a rupture. Medially of the upper barrel 11 is an outwardly extending flange 23 which is adapted to contact the flange 17 of the lower barrel 12. As shown in FIGS. 2 and 3, the hypodermic syringe may be sealed at the flanges by an elastomeric sealing ring 24; the sealing ring also prevents relative movement between the two barrels. If the slot vent is located on the inner sidewall 16, it will be sealed by the elastomer ring 24. A plunger 30 is fitted through the open end of the upper barrel 11, the piston portion 31 of the plunger providing a vent hole 32 and a plug 33.

A solid pharmaceutical 34 is contained at the bottom of lower barrel 12, and a liquid diluent and/or pharmaceutical 35 is contained at the bottom of upper barrel 11. When the liquid 35 and solid 34 are mixed, a solution 36 of the solid will be produced.

A hypodermic needle 40 mounted on a holder 41 may be provided to fit over the seal plug 13a. Just prior to use, the holder 41 is retracted and will cause the needle 40 to pierce the seal plug 13a; the solution 36 can then be injected into the patient.

It will be apparent that the hypodermic syringe 10 of this invention is adapted for in situ lyophilization in a sterile environment using only the lower barrel 12 for this purpose. As shown in FIG. 1, during the lyophilization of a material 34 in situ, the upper barrel 11 of the hypodermic syring is inserted into the sidewall 16 of the lower barrel 12 and then moved downwardly; this permits air and product moisture from the lower barrel to vent. Further insertion together of the barrels will cause sidewall 20 to abut the shoulder 14a and occlude or seal off the vent slot 21 between the inner wall 16 of the lower barrel 12 and outer wall of the upper barrel 11. Thus, when the two barrels are mated together as shown in FIG. 2, and flanges 17 and 23 contact each other, the flanges may be sealed with the sealing ring 24 and the two barrels 11 and 12 will be fixed relative to each other and also, further seal the lyophilized material 34.

If desired, as shown in FIG. 2, if the solid material 34 and liquid 35 are to be stored and sealed separately in the syringe, the liquid is placed in the upper barrel, and the plunger 30 is inserted and pushed down. This will cause air to be forced from the upper barrel 11 through the orifice 32 and unseat the plug 33. When the plug reseats, it will be difficult to accidentally move the plunger upwardly because a partial vacuum is formed above the liquid 35. As shown in FIGS. 3 and 4, when the plunger 30 is pushed further inwardly, the bottom portion 22 of the upper barrel will contact the pivot 15 and be dislodged; the solution 35 and solid 34 will then combine to dissolve the solid and form a solution 36 which can then be injected into a patient.

Accordingly, if it is desired to obtain access to the liquid 35, solid 34 or dissolved solid 36, the plunger, and upper and lower barrels 11, 12 can be individually removed in a sterile environment and the respective material can be replaced, altered, reconstituted, etc.

I claim:

1. A multiple barrel hypodermic syringe, comprising: a lower barrel having an outlet port for a hypodermic needle; an upper barrel providing a removable hypodermic plunger at its upper end and a displaceable or frangible bottom seal at its lower end, the upper barrel being adapted to contain liquids or solids therein, the upper and lower barrels being sealed from each other solely by means of the bottom seal; the upper and lower barrels being sized for sliding engagement along their respective outer and inner peripheries; one or more grooves defining vent slots which connect the lower barrel interior solely to atmosphere, the vent grooves extending along a barrel periphery to permit gas, air and moisture to escape solely to atmosphere when the barrels are partly engaged, the vent slots being occluded to seal the lower barrel and its contents from the atmosphere, when the two barrels are substantially engaged; the upper and lower barrels being adapted to contain a liquid or solid, whereby disengagement of the barrels and hypodermic plunger enables separate removal and replacement of material from its respective barrel, without contamination of material in adjacent barrels.

2. The hypodermic syringe of claim 1 in which the solid or liquid is a pharmaceutical.

3. The hypodermic syringe of claim 1 including flange members disposed on the upper and lower barrels, and adapted to contact each other when the barrels are substantially engaged; and, an elastomeric ring engaging the flanges, thereby sealing the lower barrel.

4. The hypodermic syringe of claim 1, the upper and lower barrels being partially engaged, thereby exposing a vent slot; the lower barrel containing a lyophilizable material, the said syringe being adapted for an in situ lyophilization process.

5. The hypodermic syringe of claim 1, comprising means to seal the syringe following the lyophilization process.

6. A process for the in situ lyophilization of a material, which comprises carrying out the lyophilization process in a multiple barrel hypodermic syringe, including: a lower barrel having an outlet port for a hypodermic needle; an upper barrel providing a removable hypodermic plunger at its upper end, and a displaceable or frangible bottom seal at its lower end, the upper barrel being adapted to contain liquids or solids therein, the upper and lower barrels being sealed from each other solely by means of the bottom seal; the upper and lower barrels being sized for sliding engagement along their respective outer and inner peripheries; one or more grooves defining vent slots which connect the lower barrel interior solely to atmosphere, the vent grooves extending along a barrel periphery to permit gas, air and moisture to escape during lyophilization solely to atmosphere when the barrels are partly engaged, the vent slots being occluded to seal the lower barrel and its contents from the atmosphere, when the two barrels are substantially engaged; the upper and lower barrels being adapted to contain a liquid or solid, whereby disengagement of the barrels and hypodermic plunger enables separate removal and replacement of material from its respective barrel, without contamination of material in adjacent barrels.

7. The process of claim 6 in which the lower barrel is sealed following lyophilization.

8. The process of claim 6 in which the hypodermic syringe includes: flange members disposed on the upper and lower barrels, and adapted to contact each other when the barrels are substantially engaged; and, an elastomeric ring adapted to engage the flanges, thereby sealing the lower barrel upon completion of the lyophilization process.

9. The process of claim 6 in which the lyophilized material is a pharmaceutical.

* * * * *